US00PP30386P2

(12) United States Plant Patent
Green, Jr.

(10) Patent No.: US PP30,386 P2
(45) Date of Patent: Apr. 16, 2019

(54) *CAMELLIA* PLANT NAMED 'GREEN 08-052'

(50) Latin Name: *Camellia sasanqua*
Varietal Denomination: Green 08-052

(71) Applicant: Robert M. Green, Jr., Fairhope, AL (US)

(72) Inventor: Robert M. Green, Jr., Fairhope, AL (US)

( * ) Notice: Subject to any disclaimer, the term of this patent is extended or adjusted under 35 U.S.C. 154(b) by 0 days.

(21) Appl. No.: 15/731,774

(22) Filed: Jul. 31, 2017

(51) Int. Cl.
*A01H 5/02* (2018.01)

(52) U.S. Cl.
USPC ..... Plt./245

(58) Field of Classification Search
USPC ..... Plt./245
CPC ..... A01H 5/00; A01H 5/02; A01H 6/00
See application file for complete search history.

(56) References Cited

U.S. PATENT DOCUMENTS

PP20,506 P2 * 11/2009 Green, Jr. ..... Plt./245

OTHER PUBLICATIONS

NSW *Camellia* Research Society *Camellia* Flower Forms & Sizes 2004, retrieved on Jul. 11, 2018, retrieved from the Internet at http://www.camelliasnsw.org/forms.htm, 3 pp. (Year: 2004).*

* cited by examiner

*Primary Examiner* — June Hwu
(74) *Attorney, Agent, or Firm* — Penny J. Aguire

(57) ABSTRACT

A new cultivar of *Camellia sasanqua* named 'Green 08-052', that is characterized by its strong, upright and vigorous plant habit, its large single flowers that are crimson red in color, its longer bloom season, and its high resistance to root rot and dieback.

1 Drawing Sheet

Botanical classification: *Camellia sasanqua.*
Variety denomination: 'Green 08-052'.

BACKGROUND OF THE INVENTION

The present invention relates to a new and distinct cultivar of *Camellia* plant, botanically known as *Camellia sasanqua*, 'Green 08-052'. The new cultivar will be referred to hereafter by its cultivar name, 'Green 08-052'. 'Green 08-052' is a new perennial shrub grown for container and landscape use.

'Green 08-052' was derived from an ongoing breeding program conducted by the Inventor in Fairhope, Ala. The objectives of the breeding program are to develop new cultivars of *Camellia sasanqua* with compact plant habits, vigorous growth habits, improved disease resistance, and extended bloom periods. 'Green 08-052' originated as a seedling that arose from seed planted from open pollination of *Camellia sasanqua* cultivar 'Green 98-009' (U.S. Plant Pat. No. 20,506) as the female parent in 2005 in Fairhope, Ala. The male parent is therefore unknown. The new *Camellia* was selected as a single unique plant in Fall of 2008.

Asexual propagaton of the new cultivar was first accomplished by stem cuttings by the Inventor in 2009 in Fairhope, Ala. Asexual propagation by stem cuttings has determined that the characteristics of this cultivar are stable and are reproduced true to type in successive generations.

SUMMARY OF THE INVENTION

The following traits have been repeatedly observed and represent the characteristics of the new *Camellia*. These attributes in combination distinguish 'Green 08-052' as a new and distinct cultivar of *Camellia.*

1. 'Green 08-052' exhibits a strong, upright and vigorous plant habit.
2. 'Green 08-052' exhibits single flowers that are crimson red in color.
3. 'Green 08-052' exhibits flowers that are large in size.
4. 'Green 08-052' exhibits longer bloom season (October through December) in U.S.D.A. Zone 8.
5. 'Green 08-052' exhibits a high resistance to root rot and dieback.

The female parent of 'Green 08-052', 'Green 98-009', differs from 'Green 08-052' in having a smaller plant size, flowers that are salmon-red in color and peony-form flowers that are smaller in size. 'Green 08-052' can also be compared to the *Camellia sasanqua* cultivars 'Yuletide' (not patented) and 'Bonanza' (not patented). 'Yuletide' is similar to 'Green 08-052' in having an upright plant habit and flowers that are red in color. 'Yuletide' differs from 'Green 08-052' in having smaller plant size with smaller leaves, flowers that are smaller in size with less red in color, and in being more difficult to propagate. 'Bonanza' is similar to 'Green 08-052' in having flowers that are red in color. 'Bonanza' differs from 'Green 08-052' in having a smaller plant size and less upright habit, flowers that are smaller in size and less red in color, and in having has less resistance to *Glomerella cingulata* both in the landscape and during production.

BRIEF DESCRIPTION OF THE DRAWING

The accompanying colored photograph illustrate the overall appearance and distinct characteristics of the new *Camellia*. The photograph was taken of a 4 year-old plant of 'Green 08-052' as grown outdoors in a 7-gallon container in Fairhope, Ala. The photograph provides a close-up view of a flower of 'Green 08-052'.

The colors in the photograph are as close as possible with digital photography techniques available, the color values cited in the detailed botanical description accurately describe the colors of the new *Camellia*.

DETAILED BOTANICAL DESCRIPTION

The following is a detailed description of 4 year-old plants of the new cultivar as grown ourtdoors in 7-gallon containers in Fairhope, Ala. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming habit.*—8 to 9 weeks in October through December in Fairhope, Ala.

*Plant type.*—Evergreen shrub.

*Plant habit.*—Upright, bushy, vigorous.

*Height and spread.*—An average of 2.4 m in height and 2.1 m in spread when mature in the landscape.

*Hardiness.*—At least hardy in U.S.D.A. Zone 7b to 9. Diseases and pests. — Has shown good resistance to root rot (*Phytopthora cinnamomi*) and dieback (*Glomerella cingulata*).

*Propagation.*—Stem cuttings.

*Time required for root initiation.*—An average of 40 days.

*Time required for root development.*—About 6 months to fully develop in a 3-inch container.

*Growth rate.*—Vigorous.

Branch description:

*Branch shape.*—Round.

*Branch strength.*—Strong.

*Branch color.*—Young; a blend of 154C and 165A, mature bark; a blend of 199B and N199B.

*Branch size.*—Main lateral branches; an average of 30 cm in length and 3 mm in width with secondary lateral branches a range of 8 to 20 cm in length and 2 to 3 mm in width.

*Branch surface.*—Young; finely barked, mature; finely barked, slightly rough to touch.

*Branching.*—Densely branched with an average of 4 to 6 main lateral branches and 6 to 10 secondary laterals per main branch.

Foliage description:

*Leaf shape.*—Elliptic.

*Leaf division.*—Simple.

*Leaf base.*—Cuneate.

*Leaf apex.*—Acuminate to acute.

*Leaf fragrance.*—None.

*Leaf margins.*—Serrate.

*Leaf arrangement.*—Alternate.

*Leaf attachment.*—Petiolate.

*Leaf substance.*—Thick and rubbery.

*Leaf surface.*—Upper surface; smooth and glabrous and glossy, lower surface; smooth, glabrous, and satiny.

*Leaf size.*—An average of 5.8 cm in length and 2.8 cm in width.

*Leaf aspect.*—Held at about a 45° to stem, slightly recurved.

*Leaf quantity.*—An average of 9 per branch 17 cm in length.

*Leaf venation.*—Pinnate, inconspicuous except for mid rib; upper and lower surface 146B in color.

*Leaf variegation.*—None present.

*Leaf color.*—Young and mature leaves upper surface; a color between NN137A and and 139A but darker, young and mature leaves lower surface; a NN137B.

*Petioles.*—Flattened in shape, an average of 2 mm in width and 5 mm in length, glabrous surface, 146B in color, strong and surved upwards towards stem.

*Leaf buds.*—Lanceolate in shape, an average of of 7 mm in length and 2 mm in width, NN137C in color with apex 183A, imbricate surface.

*Stipules.*—None.

Inflorescence description:

*Inflorescence type.*—Solitary.

*Flower number.*—4 to 5 per lateral stem.

*Flower fragrance.*—Slightly fragrant.

*Flower longevity.*—About one week, self cleaning.

*Flower type.*—Rotate, single.

*Flower aspect.*—Outward to slightly upright, held at an average angle of 30 to 45° from stem.

*Flower size.*—An average of 9 cm in diameter and 2.5 cm in depth.

*Peduncles.*—None, flowers are sessile to stem.

*Flower buds.*—Ovate in shape, an average of 2.8 cm in length and 2 cm in width, color; a blend 59A and 60A in color, glabrous surface, terminal arrangement.

*Sepals.*—An average of 6, ovate in shape and strongly cupped inward, imbricate, an average of 1.2 cm in length and 1 cm in width, broadly acute apex, truncate base, entire margin, color inner and outer surface; a blend of 138A and 138B with some having a thin margin of 59B and suffused at base with 59C, outer surface glandular and dull, inner surface glabrous and satiny.

*Petals.*—An average of 6, obcordate to obovate in shape, an average of 4.5 cm in length and 2.8 cm width, apex cordate, base cuneate, margins slightly undulated, color upper and lower surfaces when opening; a blend of 59A and 187A with very base 155B, color upper and lower surfaces when fully open; a blend of 59A and 61A, glabrous and velvety on upper and lower suface.

*Receptacle.*—Disk-shaped, 3 mm in diameter and 2.5 mm in depth.

Reproductive organs:

*Pistil.*—1, style is an average of 6 mm in length, 2 mm in width, position of style splitting medium, and 145C in color when opening, stigmas are four-parted with each appendage <0.5 mm in diameter and 3 mm in length, club-shaped, 145B in color, position slightly below stamens, and glandular in appearance, ovary is oblong-oval in shape with pubescent surface with long sliky hairs and 145C in color.

*Stamens.*—An average of 60, arrangement *sasanqua*, filaments; an average of 1.3 cm in length, 68A in color when young and changing to 39C, anthers; an average of 3 mm in length and 2 mm in width, and 13B in color, pollen; moderate in quantity ans 6A in color, very rare petiolate stamens; obovate-irregular in shape, a blend of 59A and 13B in color, average of 6 mm in length and 4 mm in width.

*Fruit and seed.*—None observed to date.

The invention claimed is:

1. A new and distinct cultivar of *Camellia* plant named 'Green 08-052' as herein illustrated and described.

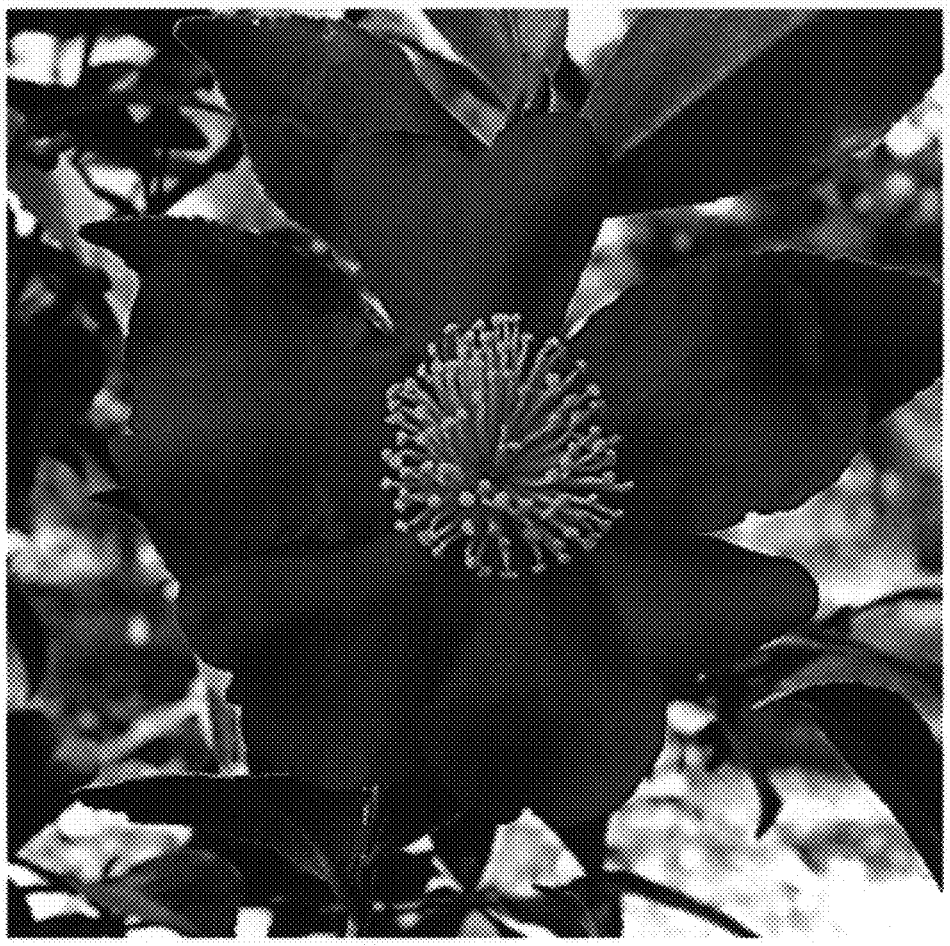

* * * * *